United States Patent [19]

Yamamoto et al.

[11] Patent Number: 5,387,209
[45] Date of Patent: Feb. 7, 1995

[54] BODY FLUID ABSORBENT ARTICLE

[75] Inventors: Masamitsu Yamamoto; Masaki Murakami; Satoshi Mizutani, all of Kawanoe, Japan

[73] Assignee: Uni-Charm Corporation, Ehime, Japan

[21] Appl. No.: 166,089

[22] Filed: Dec. 13, 1993

Related U.S. Application Data

[63] Continuation of Ser. No. 983,743, Dec. 1, 1992, abandoned.

[30] Foreign Application Priority Data

Dec. 4, 1991 [JP] Japan .................. 3-348223

[51] Int. Cl.⁶ .................. A61F 13/15; A61F 13/20
[52] U.S. Cl. .................. 604/384; 604/358; 604/366; 604/370; 604/378; 604/382; 604/383; 604/385.1
[58] Field of Search .............. 604/358, 378–385.1, 604/366, 370; 428/134, 136, 137, 161

[56] References Cited

U.S. PATENT DOCUMENTS

| | | |
|---|---|---|
| 3,929,135 | 12/1975 | Thompson . |
| 4,014,341 | 3/1977 | Karami . |
| 4,135,021 | 1/1979 | Patchell et al. .......... 604/370 |
| 4,324,247 | 4/1982 | Aziz . |
| 4,609,584 | 9/1986 | Cutler . |
| 4,634,440 | 1/1987 | Widlund . |
| 4,701,171 | 10/1987 | Boland . |
| 4,741,941 | 5/1988 | Englebert . |
| 4,762,521 | 8/1988 | Roessler . |
| 4,798,603 | 1/1989 | Meyer . |
| 4,908,026 | 3/1990 | Sukiennik .......... 604/378 |
| 4,938,753 | 7/1990 | Van Gomper . |
| 5,078,710 | 1/1992 | Suda et al. .......... 604/366 |
| 5,135,521 | 8/1992 | Luceri . |
| 5,171,238 | 12/1992 | Kejander . |

FOREIGN PATENT DOCUMENTS

| | | |
|---|---|---|
| 0040085 | 11/1981 | European Pat. Off. . |
| 0048011 | 3/1982 | European Pat. Off. . |
| 0178108 | 4/1986 | European Pat. Off. . |
| 0257280A | 3/1988 | European Pat. Off. . |
| 0336578 | 10/1989 | European Pat. Off. . |
| 0405575 | 1/1991 | European Pat. Off. . |
| 0417766 | 3/1991 | European Pat. Off. . |
| 0545423 | 6/1993 | European Pat. Off. .......... 604/370 |
| 2354064 | 1/1978 | France . |
| 0122727 | 8/1989 | Japan . |
| 0845826 | 8/1960 | United Kingdom . |
| 1160625 | 8/1969 | United Kingdom . |
| 1292133 | 10/1972 | United Kingdom . |
| 2055586 | 3/1981 | United Kingdom . |
| 2175844A | 12/1986 | United Kingdom . |
| 2225724A | 6/1990 | United Kingdom . |

Primary Examiner—Randall L. Green
Assistant Examiner—P. Zuttarelli
Attorney, Agent, or Firm—Lowe, Price, LeBlanc & Becker

[57] ABSTRACT

A body fluid absorbent article comprising a topsheet formed with tubular liquid passages extending from the bottom surface of the topsheet and an absorbent core, wherein a meshy sheet comprising fibres defining meshes smaller than lower openings of the respective liquid passages is interposed between said topsheet and said absorbent core so that said fibres extend across the lower openings (FIG. 3).

1 Claim, 4 Drawing Sheets

BODY FLUID ABSORBENT ARTICLE

CROSS REFERENCE TO RELATED APPLICATIONS

This application is a continuation of U.S. patent application Ser. No. 07/983,743, filed Dec. 1, 1992, now abandoned.

BACKGROUND OF THE INVENTION

The present invention relates to an improvement in the body fluid absorbent articles such as sanitary napkins used to absorb and thereby to hold menstrual discharge.

Body fluid absorbent articles such as sanitary napkins of prior art generally comprise a surface structure composed of a topsheet molded from thermoplastic film formed with liquid passages or channels spaced from one another in longitudinal, transverse and diagonal directions of the topsheet, each of these liquid passages or channels being opened at both upper and lower ends thereof, and an absorbent core of which the top surface is covered with the topsheet. Such surface structure can be basically classified into three types as will be described below.

One example of the first type is disclosed in Japanese Patent Application Publication No. 1982-17081. A topsheet constituting a surface structure in this patent application is molded from thermoplastic film so that a plurality of liquid passages tapered downward and their lower openings are close in contact with the top surface of an absorbent core. With such arrangement, however, if each liquid passage is tapered downward as extremely as almost to a critical diametric dimension of its lower opening beyond which a quantity of body fluid once absorbed by the absorbent core may partially flow backward again the lower openings of the liquid passages, the lower openings of the liquid passages may be blocked by a clot, assumed that the body fluid is menstrual discharge containing such clot, and no additional discharge can be smoothly transferred into the absorbent core. If the lower openings of the liquid passages are dimensioned so as to avoid this problem, the quantity of menstrual discharge having been absorbed in the absorbent core will be visible for users in a vivid shade and users may feel uncomfortable when she disposes used napkin. With the topsheet made from light-transmissive plastic film such as polyethylene film, the quantity of menstrual discharge having been absorbed in the absorbent core will be visible for users in a relatively light shade through ribs defining the upper openings of the respective liquid passages.

Another example of the first type is disclosed in Japanese Patent Application Disclosure Gazette No. 1989-249502. A topsheet forming a surface structure disclosed therein comprises a thermoplastic film layer laminated on the bottom surface of a thermoplastic fibrous layer. Since this topsheet is of two-layered structure composed of a fibrous layer and a plastic film layer, it never takes place that the quantity of menstrual discharge having been absorbed in an absorbent core is visible for users in a lighter shade through the topsheet. While this topsheet is preferred to the previously mentioned topsheet so far as the shielding effect for menstrual discharge is concerned, there remains the problem that the quantity of menstrual discharge having been absorbed in the absorbent core is visible for users in a relatively vivid shade through openings of the respective liquid passages.

One example of the second type is disclosed in Japanese Patent Application Disclosure Gazettes Nos. 1986-158954; 1989-119251; and 1990-19153. A topsheet forming a surface structure disclosed therein is molded from hydrophobic plastic film formed with liquid channels having bottoms closed and side walls opened. With such surface structure, the quantity of menstrual discharge having been absorbed in an absorbent core is not visible for users through the liquid channels. However, the closed bottoms of the respective liquid channels function as barriers preventing a sufficient quantity of menstrual discharge from being rapidly transferred to the absorbent core and clots of menstrual discharge, if any, will be apt to cling to the bottoms and stay there, resulting in that these clots are sometimes visible for users in a vivid shade.

One example of the third type is disclosed in Japanese Patent Application isclosure Gazette No. 1982-89861. A topsheet forming a surface structure disclosed therein comprises a hydrophobic meshy topsheet, a hydrophobic fibrous layer disposed on the bottom surface of said hydrophobic meshy topsheet, and a hydrophobic plastic film layer formed with tapered liquid passages and disposed on the bottom surface of said fibrous layer. This surface structure is normally effective to avoid the problem that the quantity of menstrual discharge having been absorbed in an absorbent core is visible for users through the liquid passages. However, clots of menstrual discharge, if any, may cling to fibres of the meshy topsheet as well as of the underlying fibrous layer and block the meshes, preventing a sufficient quantity of menstrual discharge from smoothly flowing into the liquid passages. In such case, menstrual discharge may be vividly visible for users just as with the above-mentioned second type of surface structure.

In view of such problems, it is a principal object of the invention to provide a surface structure for the article as mentioned in the beginning so improved that, in spite of using a topsheet formed with a plurality of liquid passages, an adequate quantity of menstrual discharge can be rapidly transferred to an absorbent core and the quantity of menstrual discharge having been absorbed in the absorbent core are substantially invisible for users.

SUMMARY OF THE INVENTION

The object set forth above is achieved, in accordance with the invention, by a body fluid absorbent article comprising a topsheet formed with liquid passages spaced from one another in longitudinal, transverse and diagonal directions, each of these liquid passages extending through the thickness of the topsheet so as to be opened at both upper and lower ends, and an absorbent core of which at least the top surface is covered with the topsheet, characterized by that a meshy sheet composed of fibres defining meshes smaller than lower openings of the respective liquid passages is interposed between the top surface of said absorbent core and the bottom surface of said topsheet in close contact with the lower ends of said liquid passages so that said fibres extend across the lower openings of the respective liquid passages and thereby divide the respective lower openings into a plurality of openings.

Preferably said meshy sheet is made of hydrophobic plastic film split into said fibres.

Preferably said fibres are further split into a plurality of finer fibres.

Preferably the lower ends of said liquid passages are bonded integrally to the top surface of said meshy sheet.

Preferably said meshy sheet is treated with suitable surfactant to make it hydrophilic.

Preferably side walls of said liquid passages are partially cut away.

Preferably said topsheet is made of hydrophobic plastic film.

The article constructed according to the invention allows menstrual discharge to be smoothly guided into the liquid passages since there exists no barrier on the top surface of the topsheet which will prevent menstrual discharge from smoothly flowing into the upper openings of the respective liquid passages. The fibres extending across the lower opening of each liquid passage are effective to attenuate or alleviate the shade in which the quantity of menstrual discharge having been absorbed in the absorbent core may be visible for users through the lower opening of the liquid passage and at the same time to suppress the possibility that the quantity of menstrual discharge having been absorbed in the absorbent core can flow back toward the top surface of the topsheet. Such functions can be proportionally improved as the number of the fibres extending across the lower opening of each liquid passage is increased.

Rapid transfer of menstrual discharge from the top surface of the topsheet to the liquid passages and therefore to the absorbent core are not obstructed by the fibres since these fibres are disposed across the lower openings of the respective liquid passages and a diameter of each opening defined by these fibres is smaller than the diameter of each liquid passage.

BRIEF DESCRIPTION OF THE DRAWINGS

The invention will be described more in detail with reference to the accompanying drawings, in which.

DESCRIPTION OF THE PREFERRED EMBODIMENTS

Figure 1:
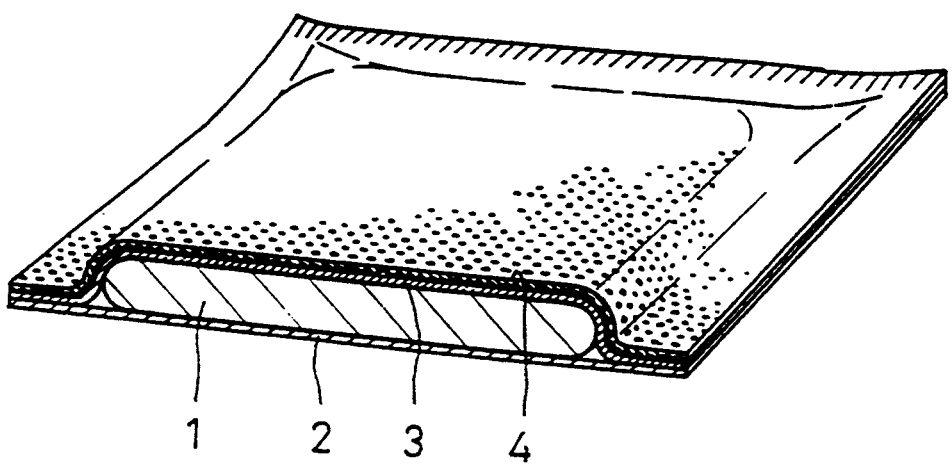
FIG. 1 is a perspective view showing an embodiment of a sanitary napkin constructed according to the invention with a portion adjacent one end thereof having been transversely cut off.
Figure 2:
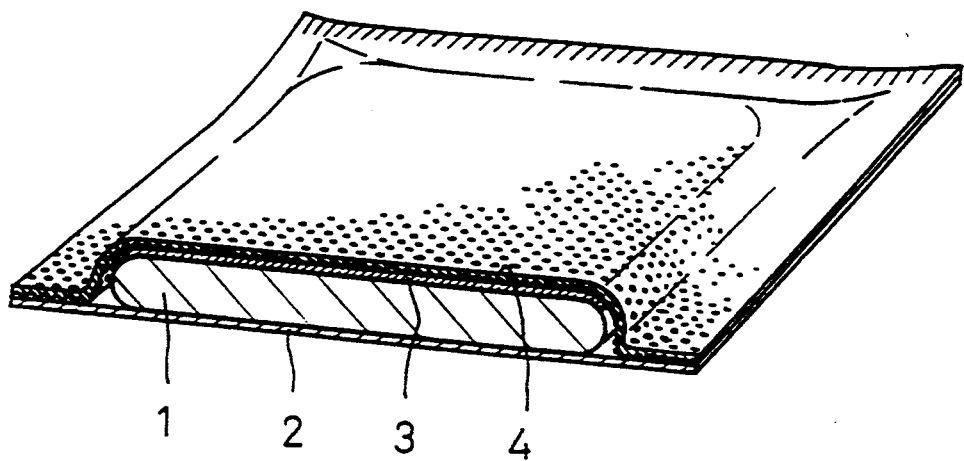
FIG. 2 is a perspective view showing another embodiment of the sanitary napkin constructed according to the invention with a portion adjacent one end thereof having been transversely cut off.

As shown by FIGS. 1 and 2, a sanitary napkin constructed according to the invention generally comprises an absorbent core 1, a liquid-impermeable backsheet 2 disposed on a bottom surface of the absorbent core 1, a meshy sheet 3 disposed on the top surface of the absorbent core 1, and a liquid-permeable topsheet 4 disposed on the top surface of the meshy sheet 4, wherein a portion of the backsheet 2 extending beyond the outer periphery of the absorbent core 1 is bonded to the corresponding portions of the meshy sheet 3 as well as to the topsheet 4 by adhesive or welding means. The napkin shown by FIG. 1 has the meshy sheet 3 covering the inner surface of the topsheet 4 in coextensive therewith while the napkin shown by FIG. 2 has the meshy sheet 3 covering only the top surface of the absorbent core 1.

Figure 3A:
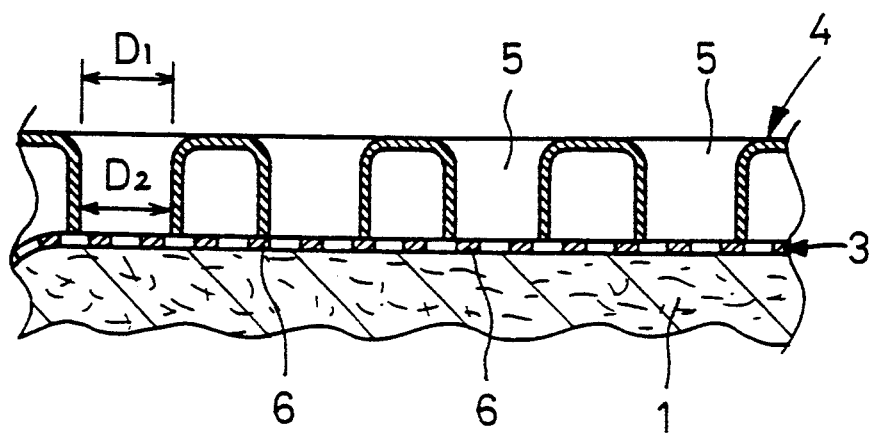
FIGS. 3A and 3B show on an enlarged scale, a part of the surface structure provided according to the invention in FIG. 3A as a sectional view and in FIG. 3B as a plan view.
Figure 3B:
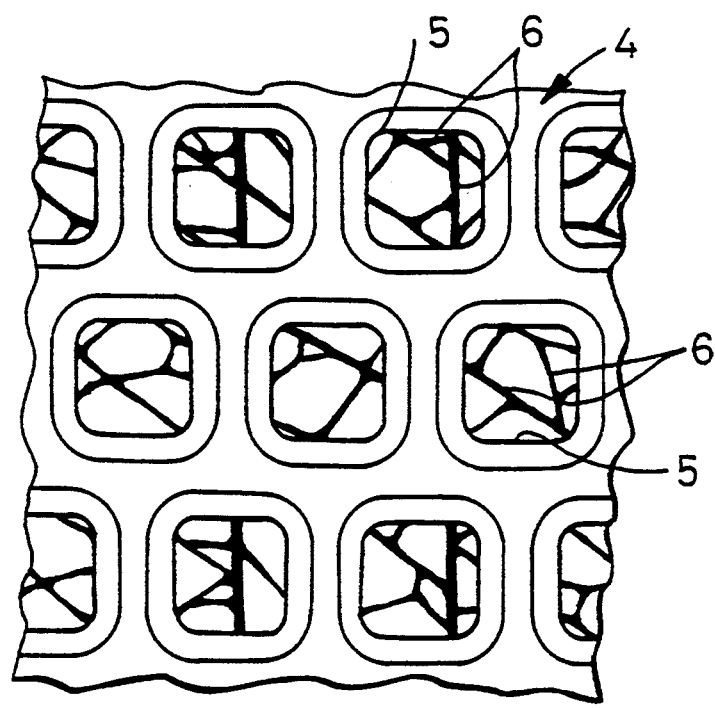
Figure 4A:
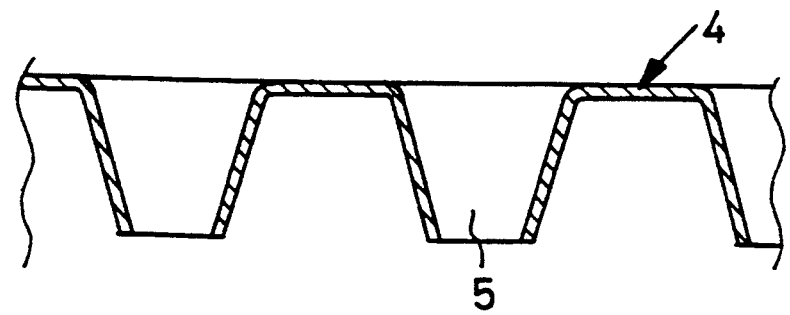
FIGS. 4(A) through 4(E) shows, in an enlarged scale, various sectional configurations of the liquid passages to be formed in the topsheet constituting a part of the surface structure provided according to the invention, respectively.
Figure 4B:
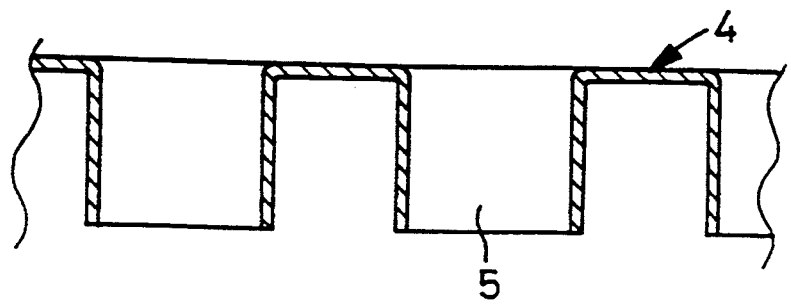
Figure 4C:
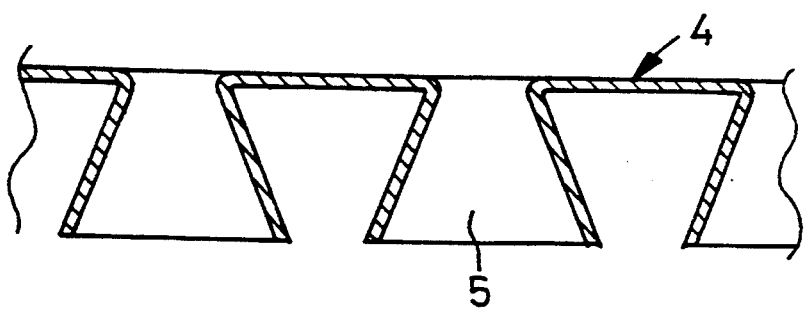
Figure 4D:
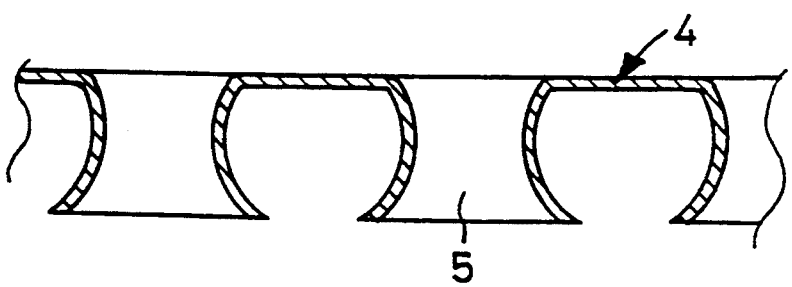
Figure 4E:
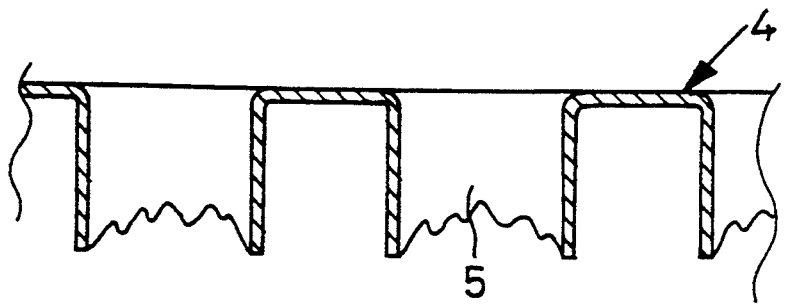

As will be apparent from FIGS. 3(A) and 3(B), the topsheet 4 is formed with liquid passages 5 spaced from one another in longitudinal, transverse and diagonal directions thereof, each of these liquid passages extending through the thickness of the topsheet 4, i.e., being opened at both upper and lower ends thereof. Each liquid passage 5 is dimensioned so that its upper opening has a diameter $D_1$ of 0.2 to 6.55 mm and its lower opening has a diameter $D_2$ of 1 to 6 mm. The sectional configuration of each liquid passage 5 is not limited to that as illustrated by FIG. 3 and may be any of those as illustrated by FIG. 4. It should be understood that the respective liquid passages 5 arranged in such manner in the topsheet 4 will effectively function even when their sectional configurations are not uniform. In such case, the above-mentioned diametrical dimensions of the upper and lower openings should be understood as the average values. The lower end of each liquid passage 5 preferably has an opening area ratio of 20 to 60%.

Such topsheet 4 can be obtained by any of the methods well known in the art, for example, a method comprising steps of placing thermoplastic film on the top surface of a mold formed with tubular openings which extend therethrough in its thickness direction and having sectional configurations corresponding to those of the respective liquid passages 5 to be formed, applying a sufficient negative pressure to the bottom surface of the mold to inflate portions of the film surrounded by upper openings of the respective tubes downward until these portions thus inflated like balloons burst at their bottoms while the film is heated up to its softening point, and finally curing the film. The bottom edge of each liquid passage 5 formed as a result of said burst under the negative pressure may be somewhat ragged depending on the particular condition of molding and, if desired, such ragged bottom edge may be trimmed off or burnt off in the well known manner. The liquid passages 5 shown by FIG. 4(E) have their side walls intentionally notched to obtain ragged lower edges.

The topsheet 4 may be made from thermoplastic material such as polyethylene, polypropyrene, EVA, nylon or styrene or a mixture thereof. Filler such as titanium dioxide or calcium carbonate of 1 to 10% by weight may be added to the thermoplastic material in order to lower a light-transmissivity thereof so as to obtain a weight per unit area of 15 to 40 g/m². If desired, the topsheet 4 may be coated with suitable surfactant or such surfactant may be mixed into the starting material of the topsheet 4.

Figure 5:
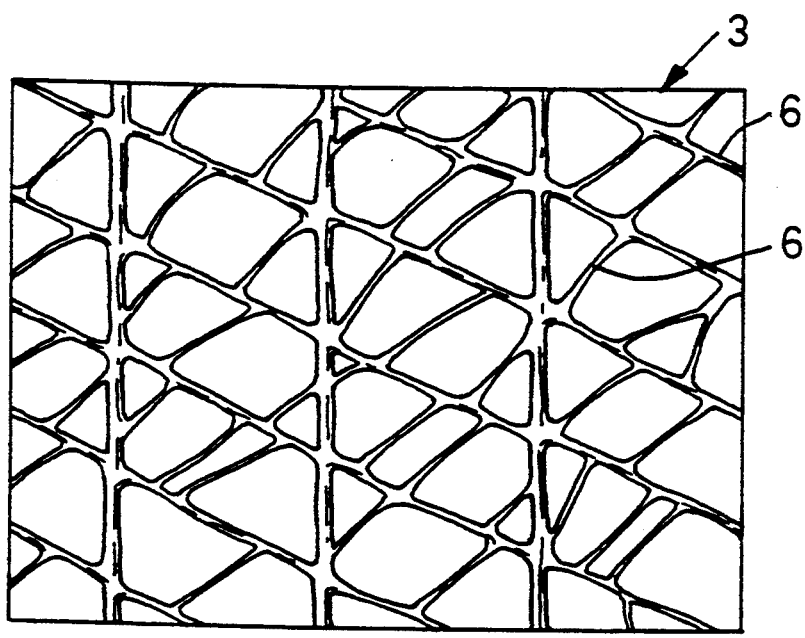
FIG. 5 is a fragmentary pan view showing, in an enlarged scale, the meshy sheet constituting a part of the surface structure provided according to the invention.

It will be apparent from FIG. 5 that the meshy sheet 3 is composed of plural fibres 6. The meshy sheet 3 can be obtained by any of the well known methods, for example, a method comprising steps of providing thermoplastic film with a plurality of slits or dot-like embosses and then splitting the film into a plurality of fibres 6 by stretching the film both in length and width with or without heating. Alternatively, the meshy sheet can be also obtained by mixing the thermoplastic resin with suitable foaming agent and then splitting this into plural fibres 6 under the effect of said foaming agent while the thermoplastic resin is extrusion-molded into film. The diameter of each opening defined by the fibres 6 must be smaller than the diameter $D_2$ of the lower opening of each liquid passage 5 and preferably less than a third of the diameter $D_2$. The fibres 6 may be further split or branched into finer fibres. Unlike a fibrous web such as nonwoven fabric in which the individual fibres are complicatedly intertwined, crossed, bonded or welded together so as to result in a relatively high weight per unit area, the meshy sheet 3 is preferably composed of the fibres 6 so arranged that substantially no liquid is held between the fibres 6. While the fibres 6 of the meshy sheet 3 are shown in an irregular arrangement, the fibre arrangement may also be in a regular pattern. If desired, the meshy sheet 3 may be treated with conventional surfactant to improve its permeability for body fluid such as menstrual discharge.

While the meshy sheet 3 may be made from the material providing the same effect as the topsheet 4, it is preferred to achieve a weight per unit area of 3 to 20 g/m² and an apparent thickness of 0.05 to 0.15 mm. It should be understood that it is difficult to make such superthin meshy sheet from fibrous web.

This meshy sheet 3 is placed under the topsheet 4 in close contact with the lower ends of the respective liquid passages 5 and, if desired, said lower ends may be partially bonded integrally to the meshy sheet 3 by adhesive or welding means. In this manner, as will be apparent from FIGS. 3(B) and 5, several fibres 6 extend across the lower opening of each liquid passage 5 so as to divide this opening into a plurality of openings. Consequently, menstrual discharge flowing into the liquid passages 5 is then transferred to the absorbent core 1 through these divided openings.

The absorbent core 1 and the backsheet 2 may be made from the material conventionally used in sanitary napkins of prior art for these components. For example, the absorbent core 1 may be made from fluff pulp mixed with superabsorbent polymer powder and, if desired, covered at least on top and bottom surfaces with liquid-permeable sheets such as tissue paper while the backsheet 2 may be made from plastic film, lamination of such plastic film and nonwoven fabric, or water-repellent or water-proof nonwoven fabric.

As has already been mentioned, the article of the invention is advantageous over the conventional article of this art in that the shade in which the quantity of menstrual discharge having been absorbed in the absorbent core may be visible for users through the openings of the liquid passages so as to eliminate uncomfortable feeling which otherwise will be given to users and the quantity of menstrual discharge having been absorbed in the absorbent core is well prevented from flowing back toward the top surface of the topsheet so as to eliminate a sense of wetting for users. The invention easily achieves such effect merely by a unique design of the liquid passages formed in the topsheet, which has been very difficult in the prior art. The article of the invention allows clots of menstrual discharge, if any, to flow into the liquid passages so far as these clots are smaller than the upper openings of the liquid passages, since the upper openings of the liquid passages are covered with no other material.

What is claimed is:

1. A body fluid absorbent article comprising a layered composite that includes (A) a topsheet (4) consisting of a thickness of hydrophobic film having an upper surface and a lower surface which between them define the thickness of the material forming the topsheet (4), said topsheet (4) comprising (a) a first portion which is generally planar and (b) a second portion which comprises a plurality of tubular passageways (5) located at spaced apart points in said first portion and which extend downwardly from said planar portion a distance which is greater than the thickness of said topsheet (4), the walls of said tubular passageways (5) being composed of portions of said topsheet that have been deformed downwardly in relation to said planar portion, the lower end of each tubular passageway (5) having a ragged edge contour, (B) a meshy sheet (3) composed of hydrophobic plastic film having an upper surface and a lower surface, said film having been treated with a surfactant to make it hydrophilic, said meshy sheet (3) being split into a plurality of spaced apart fibers (6) that define between them a plurality of mesh openings that are smaller than the openings in the lower ends of each tubular passageway (5), the upper surface of said meshy sheet (3) being bonded integrally to the lower ends of each tubular passageway (5) so that said fibers (6) will extend across the lower ends of said tubular passageways (5) to thereby divide each of said lower openings into a plurality of smaller openings, and (C) an absorbent core (1) having an upper surface and a lower surface, said upper surface being covered by the lower surface of said meshy sheet (3).

* * * * *